(12) United States Patent
Felder

(10) Patent No.: US 8,758,287 B2
(45) Date of Patent: Jun. 24, 2014

(54) UTILIZATION OF STENTS FOR THE TREATMENT OF BLOOD BORNE CARCINOMAS

(75) Inventor: Mitchell S. Felder, Hermitage, PA (US)

(73) Assignee: Marv Enterprises, LLC, Hermitage, PA (US)

( * ) Notice: Subject to any disclaimer, the term of this patent is extended or adjusted under 35 U.S.C. 154(b) by 62 days.

(21) Appl. No.: 13/128,870

(22) PCT Filed: Nov. 11, 2009

(86) PCT No.: PCT/US2009/064008
§ 371 (c)(1),
(2), (4) Date: May 11, 2011

(87) PCT Pub. No.: WO2010/056732
PCT Pub. Date: May 20, 2010

(65) Prior Publication Data
US 2011/0251544 A1 Oct. 13, 2011

Related U.S. Application Data

(60) Provisional application No. 61/148,431, filed on Jan. 30, 2009, provisional application No. 61/113,809, filed on Nov. 12, 2008.

(51) Int. Cl.
*A61M 1/36* (2006.01)
*A61M 1/00* (2006.01)

(52) U.S. Cl.
USPC ....... 604/6.09; 604/5.04; 604/5.01; 604/4.01; 435/372; 210/645; 210/203

(58) Field of Classification Search
CPC ...................................................... A61M 1/00
See application file for complete search history.

(56) References Cited

U.S. PATENT DOCUMENTS

| | | | |
|---|---|---|---|
| 4,048,064 A * | 9/1977 | Clark, III | 210/638 |
| 4,381,004 A | 4/1983 | Babb | |
| 4,787,974 A | 11/1988 | Ambrus et al. | |
| 4,950,225 A * | 8/1990 | Davidner et al. | 604/6.08 |
| 5,047,321 A | 9/1991 | Loken | |
| 5,069,662 A * | 12/1991 | Bodden | 604/5.01 |
| 5,277,820 A | 1/1994 | Ash | |
| 5,466,574 A | 11/1995 | Liberti et al. | |
| 5,514,340 A | 5/1996 | Lansdorp et al. | |
| 5,853,722 A | 12/1998 | Rollins | |
| 6,821,790 B2 | 11/2004 | Mahant | |
| 7,018,395 B2 | 3/2006 | Chen | |
| 7,410,582 B2 | 8/2008 | Bernard et al. | |
| 8,057,418 B2 | 11/2011 | Korbling | |
| 2004/0189311 A1 * | 9/2004 | Glezer et al. | 324/444 |

(Continued)

FOREIGN PATENT DOCUMENTS

| WO | WO 95/03815 A1 | 2/1995 |
|---|---|---|
| WO | WO 2013/028451 A1 | 2/2013 |

*Primary Examiner* — Leslie Deak
*Assistant Examiner* — Sara Sass

(57) ABSTRACT

A filter and a method treat blood borne carcinomas by inducing apoptosis in carcinoma cells. The filter includes comprises a stent having an interior wall defining a channel containing a packing material and at least one antineoplastic agent. The method includes placing a patient's blood in apposition of the antineoplastic agent by pumping the blood through the stent. The blood remains in apposition to the antineoplastic agent for a sufficient time period to induce an apoptotic cascade.

20 Claims, 3 Drawing Sheets

(56) References Cited

U.S. PATENT DOCUMENTS

| | | |
|---|---|---|
| 2004/0215173 A1* | 10/2004 | Kunst .................... 604/891.1 |
| 2005/0159805 A1 | 7/2005 | Weber et al. |
| 2005/0242033 A1 | 11/2005 | Tu |
| 2005/0271653 A1 | 12/2005 | Strahilevitz |
| 2006/0025713 A1 | 2/2006 | Rosengart et al. |
| 2008/0145333 A1 | 6/2008 | Lentz |
| 2008/0195024 A1 | 8/2008 | Schmid-Schonbein |
| 2009/0068194 A1 | 3/2009 | Julien |
| 2009/0191217 A1 | 7/2009 | de Wildt |
| 2010/0030196 A1 | 2/2010 | Hildebrand |
| 2011/0009312 A1 | 1/2011 | Rosen |
| 2011/0098623 A1 | 4/2011 | Zhang |
| 2011/0160636 A1 | 6/2011 | Bansal |
| 2011/0295175 A1 | 12/2011 | Felder |

* cited by examiner

UTILIZATION OF STENTS FOR THE TREATMENT OF BLOOD BORNE CARCINOMAS

FIELD OF THE INVENTION

The invention relates to a device and method for the treatment of blood borne carcinomas, particularly leukemia, and for the inhibition of carcinoma metastasis.

BACKGROUND OF THE INVENTION

The treatment of blood borne cancers with conventional therapies such as cytotoxic drugs and irradiation has not been as effective as desired. A major drawback has been that such treatments can destroy healthy as well as diseased cells.

One way to kill cancer cells is through the natural phenomenon of apoptosis, also referred to as programmed cell death. Apoptosis is a critical homeostatic mechanism in the body to maintain the necessary proportion of cell proliferation and cell death. The problem with conventional agents that induce apoptosis is that these agents also may have deleterious systemic effects.

SUMMARY OF THE INVENTION

The present invention utilizes an article and method to kill blood borne cancer cells using extracorporeal dialysis. More particularly, the invention relates to an article and method to treat a patient afflicted with a blood borne cancer, such as leukemia, by filtering the patient's blood through a filter comprising at least one extracorporeal stent treated with an antineoplastic agent. The invention induces apoptosis of leukemic cells or carcinoma cells in the patient's bloodstream.

The device can induce apoptosis of carcinoma cells and is substantially non-toxic to the patient. The method pumps a patient's blood through a filter comprising at least one stent treated with an antineoplastic agent. The method can greatly reduce the risk of deleterious side effects and morbidity and mortality to the patient.

The stent of the present invention includes an interior wall that defines a channel. The channel is configured to induce apoptosis of cancer cells. The channel can contain packing material. At least a portion of the channel can be coated with a coating comprising an antineoplastic agent.

The present invention can enhance the longevity and quality of life of patients by inducing apoptosis of the blood borne carcinoma cells by using a non-toxic filter comprising stents that induce apoptosis of cancer cells. The removal of blood borne carcinoma cells from the body of a patient can reduce complications and lessen the frequency of hospital stays and/or the need for chemotherapy. These and other aspects of the present invention will be more fully understood from the following detailed description of the invention and the drawing.

DETAILED DESCRIPTION OF THE INVENTION

The present invention comprises a device and a method that induce apoptosis in carcinoma cells. The device comprises a filter including extracorporeal stent having an interior wall defining a channel containing at least one antineoplastic agent. The channel preferably contains packing material that improves apposition of the antineoplastic agent with blood. The method comprises pumping a patient's blood through the device in order to induce apoptosis in carcinoma cells.

As used herein, a "filter" includes a leukophoretic filter, a dialysis filter, and combinations thereof. A "leukophoretic filter" means a device that selectively removes white blood cells from a patient's blood. A "dialysis filter" means a device that separates blood cells of different dimensions, such as white blood cells and red blood cells, from a patient's blood.

The filter includes at least one stent defining a channel containing at least one antineoplastic agent. Preferably, the filter includes a plurality of stents. To improve apposition, packing material can be inserted in the channel. Packing material can increase surface area within the channel, and can be fixed or unsecured to the stent. The filter can also include a pump to pump blood of the patient through the filter, a heparin/protamine injection port for administering an effective amount of heparin and protamine into the patient's blood as it circulates through the filter, a trap to prevent air bubbles from entering into the patient's bloodstream, and an arterial catheter and a venous catheter to connect the patient's vascular system to the filter.

Figure 1:
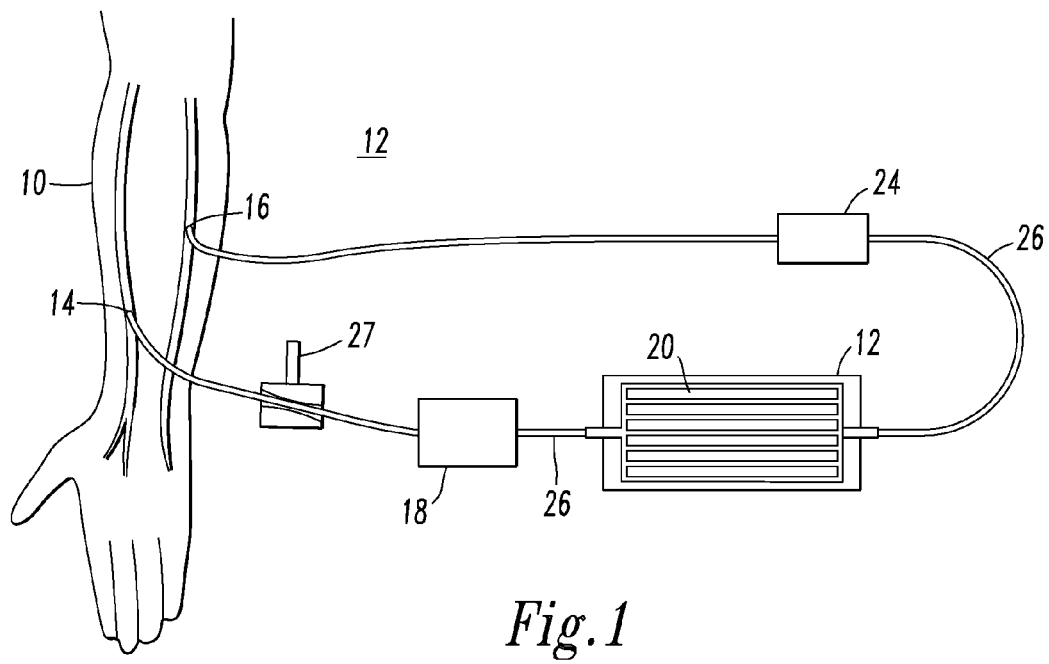
FIG. 1 shows a filtering device of the present invention attached to the vascular system of a patient.

The device of the present invention can induce apoptosis in blood borne carcinoma cells of a patient. As shown in FIG. 1, the vascular system of a patient 10 is connected to the filter 12 by inserting an arterial catheter 14 into an artery preferably located in the forearm, such as the radial artery, and inserting a venous catheter 16 into a vein preferably located in the forearm, such as the cephalic vein. The arterial and venous catheters 14, 16 can be made of any suitable tubing commonly used in the art for such purposes, such as plastic. The patient's blood from the arterial catheter 14 is pumped through tubing 26 to the filter 12 by a pump 18 which pumps the blood through the filter 12. Tubing 26 exiting the filter 12 carries the blood back to the venous catheter 16. The filter 12 includes at least one stent 20 and preferably a plurality of stents. The stent 20 comprises an inner wall 21 defining a channel.

Figure 3:
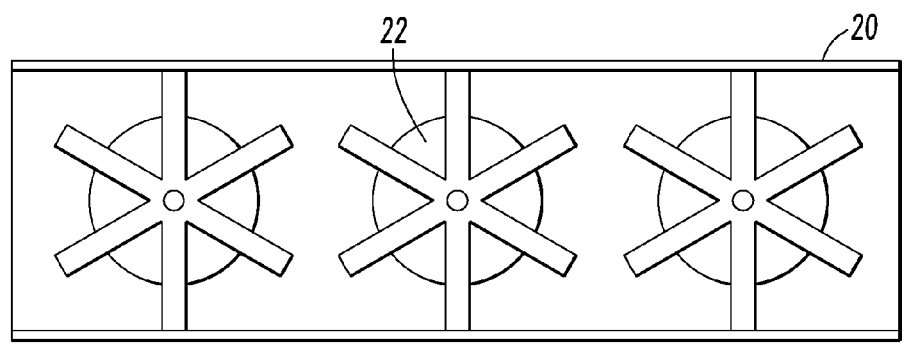
FIG. 3 shows a cross-section of an alternative embodiment of the stent.
Figure 2:
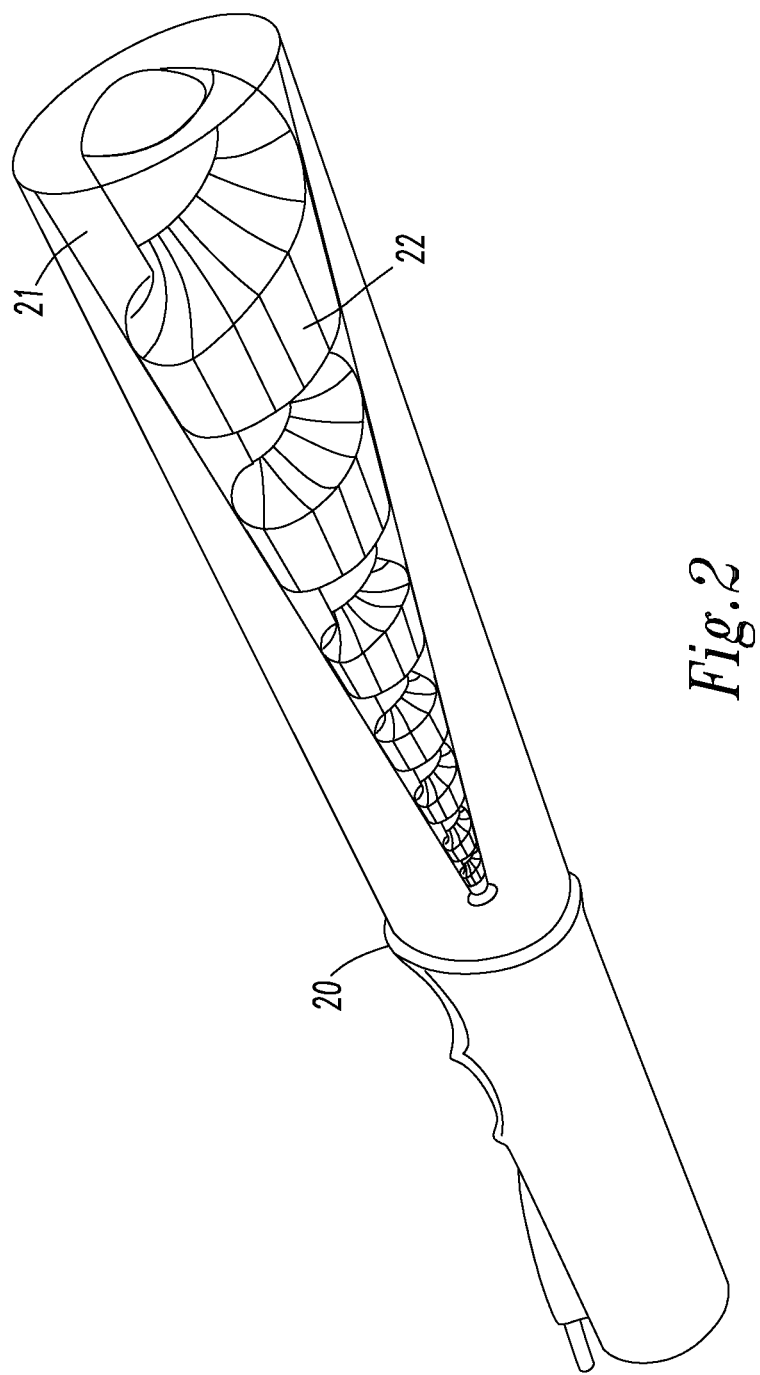
FIG. 2 shows a perspective view of a stent of the present invention with a portion of the exterior removed.
Figure 4:
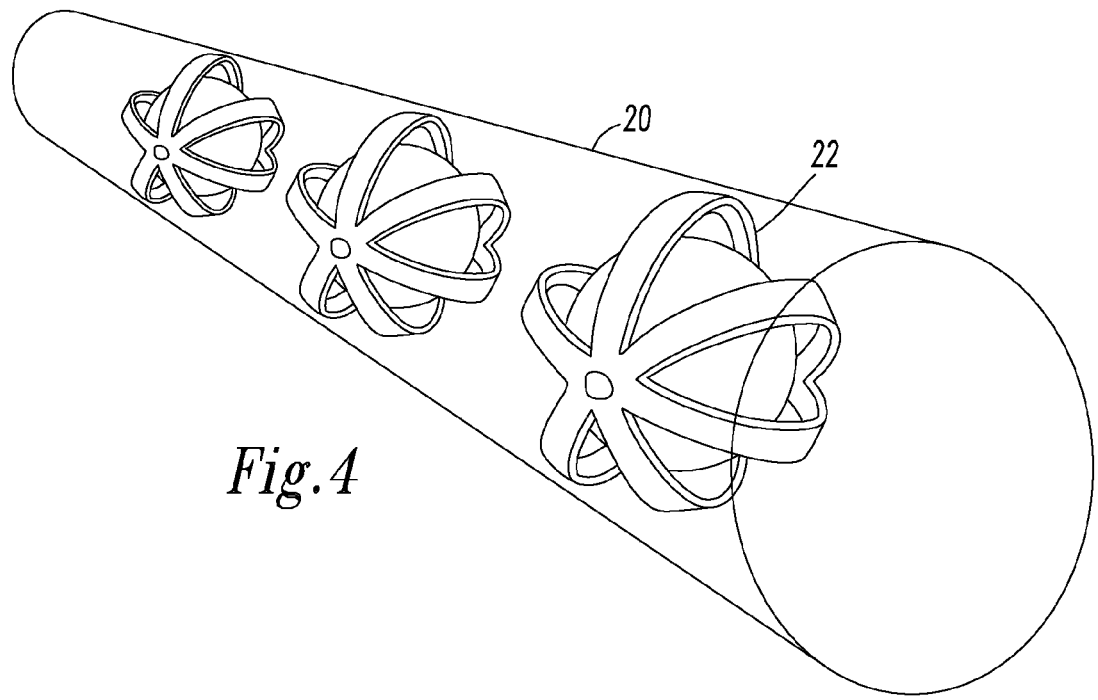
FIG. 4 shows a perspective view of the stent of FIG. 3.
Figure 5:
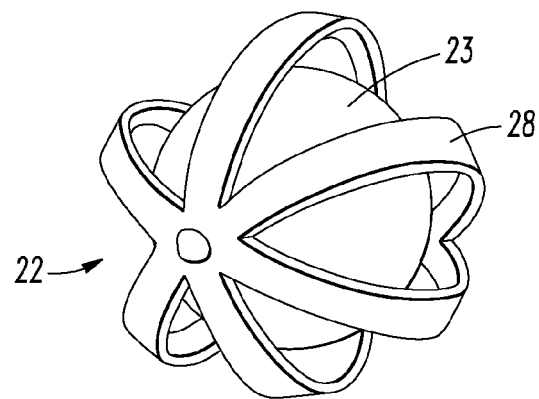
FIG. 5 shows a packing material of the stent of FIG. 3.

Packing material 22 can be placed within the channel in order to increase the surface area within the channel that is available for apposition with the blood. Packing material can include helixes, rods, spheres, discs, sheets, and other shapes. U.S. Pat. No. 4,072,736 is hereby incorporated by reference. One skilled in the art would appreciate the variety of packing materials that could be used in the present invention. In embodiments, the stent 20 can include packing material 22 as shown in FIG. 3-5. The packing material 22 can include, for example, a sphere 23 within a cage 28.

At least a portion of the channel and/or packing material includes an antineoplastic agent. The antineoplastic agent is typically applied as a coating but it may be incorporated into the body of the interior wall or packing material. In embodiments, interposed between the arterial catheter 14 and the pump 18 is a heparin/protamine injection port 27 to add an effective amount of heparin to the patient's blood in the tubing 26 to keep it from coagulating as it circulates through the filter and tubing 26. After treatment is completed, an effective amount of protamine is added to the patient's blood in the tubing 26 to reverse the anticoagulant effect of the heparin. Additionally, interposed between the filter 12 and the venous catheter 16 is a trap 24 to prevent any bubbles from entering the patient's bloodstream.

In embodiments, at least a portion of the inner wall and/or packing material includes an antineoplastic agent, which is typically dispersed as a coating. The coating is preferably dispersed evenly on the surface of the channel. The total surface area of a channel will be at least about $0.1 \text{ mm}^2$, and preferably from at least about $0.1 \text{ mm}^2$ to about $1.0 \text{ mm}^2$. The channels with or without packing material will have a diameter sufficient to permit blood to pass. The diameter can be conveniently from between about 5 mm to about 2 cm and preferably around about 1 cm. The stent can comprise any suitable material, such as for example and without limitation, plastics and glass. In embodiments, the channels comprise polyurethane.

The antineoplastic agent comprises any chemical capable of inducing cell death including, for example, paclitaxel, sirolimus, taxol, polymethyldisiloxane, polycaprolactone, polyethylene glycol, polylactic acid, ethylene vinyl acetate, and combinations thereof. Other antineoplastic agents include but are not limited to the group consisting of Dactinomycin, Davnomycin, Altretamine, Asparginase, Busulfan, Carboplatin, Hydroxyurea, Interferon alfa, Leucovoran, Melphalan hydrochloride, Lomustine, Fluorouracil, Goserelin, Megestrol, L-Sarcolysin, Mechlorethamine, Idarubicin, Ifosfamide, Isophosphamide, Leuprolide, Levamisole, Vincristine, Methotrexate, Mitomycin, Flutamide, Floxuridine, Doxorubicin, Etoposide-epipodophyllotoxin, Fludarabine, Irinotecan, Vinorelbine tartrate, Thiotepa-triethylene, thiophosphoramide, G-Thioguanine, Tamoxifen, Mitoxantrone, Mercaptopurine, Paclitaxel, Procarbazine, Vinblastine, Plicamycin-Mithramycin, Streptozocin, Streptozotocin, Bisulfan, Allopurinol sodium, Cisplatin, Cyclophosphamide, Temozolomide, Melphan hydrochloride, Epirubicin, Bleomycin, Cytarabine-cytosine arabinoside, Cladribine, Carmustine, Bleomycin sulfate, and combinations thereof.

In embodiments, the channel can also include cell adhesion molecules (CAMS) in order to selectively attract the blood borne cancer or leukemic cells. Conveniently, the CAMS can be applied as a coating. The CAMS can place cancer cells in apposition to the antineoplastic agent for a greater length of time. The channels can also include antibodies that attack leukemic and/or cancer cells. The antibodies can be anchored to the channel surfaces, including the inner wall and packing material.

The method of the present invention comprises treating a patient's blood excorporeally with an antineoplastic agent. In embodiments, the method includes passing a patient's blood through a filter as described, thereby exposing it to the antineoplastic agent. The method can include removing blood from a patient's vascular system, injecting an effective amount of heparin into the patient's blood to prevent coagulation, pumping the blood to the filter, exposing the blood to the antineoplastic agent for an effective period of time wherein the blood borne carcinoma cells present in the patient's bloodstream undergo apoptosis, injecting an effective amount of protamine into the heparin/protamine injection port to reverse the action of heparin after treatment is completed, and returning the blood to the patient's vascular system. The effective period of time that a patient is treated according to the methods of the present invention can range from between about two to about sixty minutes, preferably about fifteen minutes.

Sufficient apposition of the blood with the antineoplastic agent can affect treatment time. Factors affecting apposition include, for example, the type and quantity of packing material and the residence time of the patient's blood in the channel. Packing material increases the surface area within the channel and preferably does not significantly hinder blood flow. Residence time can be altered by passing the patient's blood through the filtering device several times so as to increase the time that the patient's blood is in contact with the channel, or by decreasing flow rate of the patient's blood through the filtering device.

The method of the present invention includes passing a patient's blood through a stent having a channel containing an antineoplastic agent. The method includes inducing a sufficient apposition of the antineoplastic agent with anaplastic leukemic cells or carcinoma cells. Apposition is performed for a time period sufficient to induce an apoptotic cascade. The apoptotic cascade is induced by forcing the leukemic and/or metastasizing carcinoma cells in close apposition to antineoplastic agents.

Optionally, blood in the stents can be centrifuged at a velocity that will increase apoptosis without substantially lysing the nonanaplastic cells. The method can also comprise extracorporeal irradiation of the patient's blood as it flows through the filter. Irradiation can preferentially destroy cancer cells in the patient's blood. The type of irradiation can include, but is not limited to, gamma radiation. The dose of radiation can range from between about 10 to about 3000 rads, and is preferably about 100 rads.

The method can further comprise heating or cooling the patient's blood as it flows through the filtering device. Heating can be accomplished by any suitable heating device known in the art, in which the heating device raises the temperature of the patient's blood as it flows through the filter. Cooling can be effected by any suitable cooling means known in the art, such as, without limitation, dry ice or refrigeration. The heating and cooling device each is directed towards or applied to the channel of the filtering device.

In another embodiment of the present invention, a method is provided for treating blood borne carcinoma cells. The method includes connecting the vascular system of a patient to a filter comprising a stent having a channel treated with a desiccated antineoplastic agent. Desiccated means finely powdered and/or freeze dried. Antineoplastic agents include, but not be limited to, the group consisting of Dactinomycin, Davnomycin, Altretamine, Asparginase, Busulfan, Carboplatin, Hydroxyurea, Interferon alfa, Leucovoran, Melphalan hydrochloride, Lomustine, Fluorouracil, Goserelin, Megestrol, L-Sarcolysin, Mechlorethamine, Idarubicin, Ifosfamide, Isophosphamide, Leuprolide, Levamisole, Vincristine, Methotrexate, Mitomycin, Flutamide, Floxuridine, Doxorubicin, Etoposide-epipodophyllotoxin, Fludarabine, Irinotecan, Vinorelbine tartrate, Thiotepa-triethylene, thiophosphoramide, G-Thioguanine, Tamoxifen, Mitoxantrone, Mercaptopurine, Paclitaxel, Procarbazine, Vinblastine, Plicamycin-Mithramycin, Streptozocin, Streptozotocin, Bisulfan, Allopurinol sodium, Cisplatin, Cyclophosphamide, Temozolomide, Melphan hydrochloride, Epirubicin, Bleomycin, Cytarabine-cytosine arabinoside, Cladribine, Carmustine, Bleomycin sulfate, and combinations thereof.

Preferably, a treatment is tailored to the specific cancer being treated. Examples would include, but not be limited to:

| Coating in Channel Tube | Cancer Being Treated |
|---|---|
| Busulfan | Chronic Myelogenous Leukemia |
| Temozolomide | Anaplastic Astrocytoma |
| Melphalan Hydrochloride | Multiple Myeloma |

As the patient's blood flows through the filter, the cancer cells in the patient's blood undergo apoptosis. The effective period of time that a patient is treated according to the methods of the present invention can range from between about two to about sixty minutes, and is preferably about fifteen minutes.

In further embodiments, the method comprises extracorporeal irradiation of the patient's blood as it flows through the filtering device in order to destroy cancer cells in the patient's blood. The type of irradiation can include, but is not meant to be limited to, gamma, radiation. The dose of radiation can range from between about 10 to 3000 rads, preferably about 100 rads. The method can also comprise heating or cooling the patient's blood as it flows through the filter. Heating can be effected by using any heating device known in the art, in which the heating device raises the temperature of the patient's blood as it flows through the filter. Cooling can be effected by any cooling means known in the art, such as, without limitation, dry ice. The heating and cooling device each are directed towards or applied to the channels of the filtering device. It is believed, without being bound by the theory, that heating or cooling of the patient's blood as it flows through the filtering device enhances apoptosis of the patient's cancer cells.

The antineoplastic agents coating the surface of the channels of the present invention are not selective in their induction of apoptosis; they induce apoptosis in all cells that they contact. Nevertheless, similar to conventional chemotherapy and radiation therapies for cancer, a greater number of cancer cells are destroyed than normal cells. More importantly, however, is that the methods of the present invention have the added advantage that the destruction of cells is effected by a local, non-toxic mechanism with only those cells in contact with the antineoplastic agents being destroyed. In embodiments, the central mechanism of apoptosis involves fragmentation of DNA. Therefore, cell which lack nuclear material are not vulnerable to apoptosis such as mature red blood cells. Therefore, in the present invention, mature red blood cells do not under apoptosis and will flow through the filter and re-enter the patient unharmed.

The blood borne carcinoma cells that are killed by induction of apoptosis according to the methods of the present invention are not removed from the filter but are returned back into the circulation of the patient. Rather than being harmful to the patient, the dead carcinoma cells returned to the patient are phagocytized, as normally would occur when cells undergo apoptosis. Additionally, no inflammation accompanies this process.

Numerous modifications and variations of the present invention are possible. It is, therefore, to be understood that within the scope of the following claims, the invention may be practiced otherwise than as specifically described. While this invention has been described with respect to certain preferred embodiments, different variations, modifications, and additions to the invention will become evident to persons of ordinary skill in the art. All such modifications, variations, and additions are intended.

The invention claimed is:

1. A filter comprising at least one extracorporeal stent comprising an interior wall defining a channel containing at least one antineoplastic agent for treating blood borne carcinomas in a patient in need thereof; wherein the channel includes a packing material that increases surface area within the channel, and the packing material has a shape selected from the group consisting of a helix, rod, sphere, disc, sheet, caged sphere or combinations thereof.

2. The filter of claim 1, wherein the antineoplastic agent is selected from the group consisting of paclitaxel, sirolimus, taxol, polymethyldisiloxane, polycaprolactone, polylactic acid, ethylene vinyl acetate, and combinations thereof.

3. The filter of claim 1, wherein a coating on the interior wall comprises the at least one antineoplastic agent.

4. The filter of claim 1, wherein the interior wall defines a surface area of at least about 0.1 $mm^2$.

5. The filter of claim 1, wherein the channel includes a diameter from about 5 mm to about 2 cm.

6. The filter of claim 1, wherein the channel includes a cell adhesion molecule that selectively attracts blood borne carcinoma cells.

7. The filter of claim 1, wherein the channel includes an antibody that attaches to blood borne carcinoma cells.

8. The filter of claim 1, wherein the channel includes a packing material that increases surface area within the channel.

9. The filter of claim 8, wherein the packing material shape is selected from the group consisting of a helix, rod, sphere, disc, sheet, caged sphere, and combinations thereof.

10. The filter of claim 8, wherein the packing material including a cell adhesion molecule or antibody.

11. The filter of claim 1, wherein the filter comprises a filter selected from the group consisting of a leukophoretic filter, a dialysis filter, and combinations thereof.

12. The filter of claim 1, wherein the filter includes a plurality of stents.

13. The filter of claim 1, wherein the filter comprises a pump to pump blood through the filter.

14. The filter of claim 13, wherein the filter comprises a heparin/protamine injection port for administering an effective amount of heparin and protamine into the blood as the blood circulates through the filter.

15. The filter of claim 13, wherein the filter comprises a trap to remove air bubbles from the blood.

16. The filter of claim 1, wherein the filter comprises an arterial catheter and a venous catheter, whereby the filter connects to a patient's vascular system.

17. A method for treating blood borne carcinoma cells comprising: passing a patient's blood through a filter including at least one extra-corporeal stent comprising an interior wall defining a channel containing at least one antineoplastic agent; and inducing a sufficient apposition of carcinoma cells with the antineoplastic agent to induce an apoptotic cascade.

18. The method of claim 17, further comprising centrifuging the patient's blood at a velocity that will increase apoptosis without substantially lysing nonanaplastic cells.

19. The method of claim 17, further comprising extracorporeally irradiating the patient's blood.

20. The method of claim 17, further comprising heating or cooling the patient's blood.

\* \* \* \* \*